Figure 1:
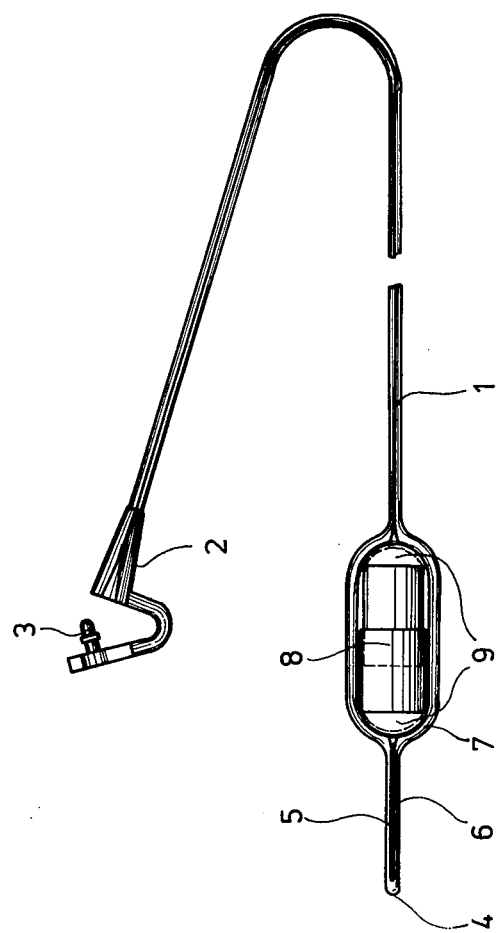

United States Patent [19]

Rüsch

[11] 4,279,251
[45] Jul. 21, 1981

[54] TUBE FOR ENTERAL TREATMENT

[75] Inventor: Heinz Rüsch, Waiblingen, Fed. Rep. of Germany

[73] Assignee: Willy Rusch GmbH & Co. KG, Kernen i.R., Fed. Rep. of Germany

[21] Appl. No.: 45,803

[22] Filed: Jun. 5, 1979

[30] Foreign Application Priority Data

Jun. 7, 1978 [DE] Fed. Rep. of Germany ....... 2824893

[51] Int. Cl.³ .............................................. A61M 25/00
[52] U.S. Cl. .................................... 128/348; 128/260
[58] Field of Search ................................ 128/348–350, 128/749, 1.2, 260, 276

[56] References Cited

U.S. PATENT DOCUMENTS

| 2,773,502 | 12/1956 | Kaslow et al. | 128/260 |
| 3,395,710 | 8/1968 | Stratton et al. | 128/350 |
| 3,528,429 | 9/1970 | Beal et al. | 128/260 |

Primary Examiner—John D. Yasko
Attorney, Agent, or Firm—William D. Hall

[57] ABSTRACT

In a tube for the enteral introduction or aspiration of gases or liquids, in particular for the enteral alimentation of patients, a weighting means is affixed in the introduction end section, the said weighting means being formed of a capsule (8) which is insoluble in the stomach, but soluble in the region of the intestine. In this manner, the tubing forming the tube can be very thin.

9 Claims, 1 Drawing Figure

TUBE FOR ENTERAL TREATMENT

This invention relates to a tube for the enteral introduction or aspiration of gases or liquids, in particular for the enteral alimentation of patients, which at its introduction end is provided with a weighting means.

In an already known tube of this type, made of single-lumened tubing, a weighting means that has the form of a balloon filled with liquid is provided. In the terminal section of the tubing, the tube is provided with valves which open when an overpressure obtains within the tube and which close when within the tube a negative pressure prevails. In general, this tube is introduced via the nose and can be passed out of the stomach into the duodenum and from there into the small intestine. When the tip of the tube has reached the desired location within the small intestine, the balloon is emptied through the tube in order, in this way, to prevent the peristaltic activity of the small intestine from exerting too great a tension on the tube. (German Published Patent Application Ser. No. 24 02 573). The construction of this tube is, however, relatively complicated owing to the required valves from the tube to the outside, or from the balloon to the inside of the tube. Also of disadvantage is the fact that the balloon remains attached to the tube and, even in the empty state, disturbingly large tensile forces might possibly be transmitted to the tube.

Double-lumened intestinal tubes are also known, the one lumen forming the connection with the intestine, and the other lumen the connection with the balloon. Double-lumened tubes can, however, not be made as thin as single-lumened tubes, with the result that, with two-lumened tubes, the danger of tissue necrosis is greater.

The objective of the present invention is to provide an improved tube of the type mentioned initially, which on the one hand can be realized inexpensively and, on the other hand, permits reliable introduction and advancement to the desired location, and which, finally, after its introduction, presents the desired minimum surface of attack to any tensile forces obtaining.

This objective has been realized by the instrument of this invention by attaching to the introduction end of a tube of the type mentioned initially a weighting means taking the form of a capsule which is insoluble in the stomach, but soluble in the region of the intestine.

In this surprisingly simple manner, the instrument permits complete compliance with the requirements which, actually, are mutually exclusive. On the one hand, the weighting means in the form of the capsule, is present for as long as it is needed, namely, during the introduction and passage, and, on the other hand, it dissolves completely and disappears when it is no longer required namely, a short time after reaching the small intestine. In this way, a tube for the enteral treatment of patients with virtually ideal properties has been produced. The tubing that forms the tube can be made to be very thin, so that it gives rise to no tissue necrosis (pressure necrosis), even after long in-dwelling times. Owing to the shape and weighting of the capsule, the introduction and passage presents no problems. Over and beyond this, in a particularly preferred embodiment of the invention, the capsule is located at a short distance from the introduction end of the tube and the end of the tube is made to be opaque to X-rays. For this purpose, the end of the tube is filled either with an appropriate granulated material or powder, or even with a small metal rod, which fact permits the position of the introduced tip of the tube to be localized within the body of the patient.

The capsule can be composed entirely of material that will dissolve in the juices of the small intestine.

A capsule made only of gelatine and a varnish soluble in an alkaline environment is, in general too light, however, and, for this reason, in the preferred embodiments, the capsule is filled with a physiologically innocuous material having a greater density. When selecting the filling material, consideration is also paid to ensuring that it provides good X-ray contrast. For this facilitates the localization of the end of the tube, since the capsule can be recognized on an X-ray fluorescent screen considerably more easily than can the relatively thin tip. Preferentially, the capsule is filled with barium sulphate. This material has the desired properties and the tubes provided with a capsule filled with barium sulphate can be passed relatively easily out of the stomach and into the duodenum, from whence they can be passed into the small intestine, where the capsule dissolves, this being the case after some 15 to 30 minutes, this time largely depending upon the nature and thickness of the varnish surrounding the capsule.

The attachment of the capsule to the tubing forming the tube, can be effected in a variety of different ways. Special preference is given to an embodiment, in which the tubing forming the tube is split longitudinally in the region of the capsule and the capsule retained in the loop formed by the splitting. Here, the capsule has the form of a cylinder, to each end of which somewhat dome-shaped "caps" are fitted; the cylinder is affixed within the loop in such a way that its longitudinal axis corresponds with that of the tubing; the two halves of the tubing, which together form the loop, thus approximate longitudinally to the cylinder surface lines of the capsule.

The tubing is made of an elastic material, preferentially of silicone rubber, and the capsule could be retained within the loop by inherent elastic forces alone. A mode of attachment offering a greater degree of security is, however, in accordance with the preferred embodiments, obtained by securing the capsule in the loop by an additional coating of varnish, applied in the liquid state and then drying, the said varnish being soluble in the small intestine. In its practical effects, the varnish locks the capsule securely in place. The application of the varnish can be effected, for example, by dipping in the liquid varnish. At the same time, this application of varnish can serve to cover the capsule, which, in general, is made of gelatine, with a layer of varnish that is soluble only enterally, so that one step in the fabrication process is saved.

In a preferred further improvement of the invention, a drop of a plastics material that hardens to form an elastic mass, is applied, in the terminal regions of the loop, in which the two halves of the tubing unite again, this said mass forming a kind of small cap at the ends of the capsule and providing a secure fixation of the capsule in the tube.

By way of example, a small drop of silicone rubber adhesive can serve this purpose. These two small drops at the ends of the capsule remain on the tube when the capsule has dissolved; they are, however, so small that they do not lead to any displacement of the tube owing to peristalsis.

The tube of this invention can remain in-dwelling, not only for days, but for weeks, or even months, a fact that is of particular significance for treatments lasting for long periods, since it is then no longer necessary to introduce a new tube at regular intervals.

Further details and improvements of the present invention are to be found in the following description of one embodiment, which is also represented in the drawing, when read in conjunction with the claims.

In the drawing, a tube of the invention is represented, enlarged, in longitudinal section.

The tube represented comprises a length of tubing made of silicone rubber, 1, having an outside diameter of some 1 to 3 mm, and a length of some 1.5 meters. At the extreme end, a closure cap comprising a funnel, 2, and a closure spigot, 3, is fitted. At the opposite, introduction end of the tube, the tubing is closed by means of a hemispherically shaped rounding, 4, and the neighbouring end section of the tube, 5, is provided with a filling, 6, over a length of about 1 to 3 cm, this filling consists of a small metal rod or a strongly X-ray shadow-producing plastic rod or a powder or granulated material of high or complete impermeability to X-rays. Adjacent its end, 6, the tubing, 1, forming the tube, is split longitudinally and the two halves of the tubing, 7, which together form a loop, enclose a capsule, 8, which is filled with a physiologically innocuous material that is opaque to X-rays, for example, barium sulphate or highly pure bismuth oxide. The capsule, 8, and, if required, the halves of the tubing, 7, forming the loop, are covered with a coating of varnish that is enterally soluble, but insoluble within the stomach. In addition, a sort of a cap, 9, is preferably formed in the regions of the ends of the capsule, 8, by the application of a drop of a plastics material which, on hardening forms an elastic mass; the said cap representing an additional secure support for the capsule, 8, and thus providing the capsule, 8, with a very reliable fixation means.

When the introduction end of the tube has been passed into the small intestine, the capsule, 8, dissolves and the two halves of the tubing, 7, approximate closely to each other again, so that the tube experiences only a small tensile force due to peristaltic activity, which is not large enough to lead to an undesired displacement.

It goes without saying that the invention is not restricted to the embodiment represented here, but that deviations are possible, without exceeding the scope of the invention. In particular, individual characteristics or features of the invention can be used either alone or combined severally. For example, capsules varying in dimensions and shape can be employed. Also, the fixation of the capsule can be effected in another manner. For example, it could also be sufficient to glue the capsule with one dome-shaped cap end to the tubing, 1, and to shape the capsule itself in such a way that it permits easy introduction, for example, by giving it a shaped end, 5. In such a version, admittedly, a disadvantage would be that, after dissolution of the capsule, the end of the tube would no longer be detectable by means of X-rays. This problem could, however, be resolved, for example, by metallizing the end of the tubing in proximity to the capsule, for example, by means of cathodic evaporation or the application of a very thin-walled sheathing or a metal foil. Also, a small metal rod or an appropriate filling could be provided and closed off at both ends. A lateral opening in the tubing in the vicinity of the side of the filling facing away from the enteral end of the tube could, in this case, form the access to the intestine.

What we claim is:

1. A device for introducing fluid into or aspiring fluid from the intestines of a person comprising:

elongated means for transmitting the fluid between a location at or near an opening in the head and the intestines, said elongated means including:

(a) an elongated tube adapted to be passed through an opening that passes from the head to the intestines, said tube having a forward introduction end for entering the intestines and a rear end located near the opening in the head when the forward introduction end is inside the intestines, said fluid passing through said tube between the rear end and the forward introduction end, (b) capsule means for adding weight at or near said forward introduction end to promote movement of said forward introduction end towards the intestines when said tube is inserted into a person, the improvement comprising:

said capsule means comprising means that is not soluble in the stomach, but is soluble in the intestines, so that the capsule means largely dissolves when, but not before, said capsule means reaches the intestines.

2. A device according to claim 1 wherein the diameter of said tube is not greater than 3 millimeters whereby said tube can be left continuously in the intestines for at least one month without complications.

3. A device according to claim 1 wherein said capsule is supported by said tube a short distance from said forward introduction end in a direction along said tube towards said rear end, and wherein a portion of said forward introduction end of said tube is comprised of a material opaque to X-rays.

4. A device according to claim 3 wherein said opaque material is a metal.

5. A device according to claim 3 wherein said tube splits into two tubes at a first location near said forward introduction end of said tube, said two tubes rejoining at a second location between said first location and said forward introduction end, whereby said second and said third tubes from a loop, wherein said capsule is held in place during the insertion of said tube into a person.

6. A device according to claim 5 wherein said capsule is secured in said loop by a layer of varnish which is applied in a liquid state onto said capsule and said loop when said capsule is within said loop, whereby said layer of varnish dries and hardens to secure said capsule to said loop, wherein said varnish is soluble in the fluids contained in the intestines.

7. A device according to claim 5 wherein drops of a plastics material are applied to the ends of said capsule and to the first and second locations when said capsule is within said loop, whereby said plastics material hardens into a cap-like elastic mass on the ends of said capsule, securing said capsule to said tubes.

8. A device according to claim 1 wherein the capsule is filled with filling comprised of physiologically innocuous material.

9. A device according to claim 8 wherein the filling of the capsule comprises a material that is opaque to X-rays.

* * * * *